United States Patent [19]

Desai et al.

[11] Patent Number: 5,653,972
[45] Date of Patent: Aug. 5, 1997

[54] PRESERVED OPHTHALMIC DRUG COMPOSITIONS CONTAINING POLYMERIC QUATERNARY AMMONIUM COMPOUNDS

[75] Inventors: Suketu Dipakbhai Desai; Diane S. Nelms, both of Fort Worth, Tex.

[73] Assignee: Alcon Laboratories, Inc., Fort Worth, Tex.

[21] Appl. No.: 700,960

[22] Filed: Aug. 21, 1996

Related U.S. Application Data

[62] Division of Ser. No. 340,763, Nov. 16, 1994.

[51] Int. Cl.$^6$ .............................. A61K 9/08; A61K 31/74
[52] U.S. Cl. ..................... 424/78.04; 424/405; 424/422; 424/427; 514/772.3; 514/912; 514/954
[58] Field of Search ..................... 424/405, 78.04, 424/422, 427; 514/772.3, 912, 954

[56] References Cited

U.S. PATENT DOCUMENTS

| | | | |
|---|---|---|---|
| 3,931,319 | 1/1976 | Green et al. | 260/567.6 |
| 4,027,020 | 5/1977 | Green et al. | 424/248.56 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,407,791 | 10/1983 | Stark | 424/80 |
| 4,525,346 | 6/1985 | Stark | 424/80 |
| 4,822,819 | 4/1989 | DeSantis et al. | 514/530 |
| 4,822,820 | 4/1989 | DeSantis et al. | 514/530 |
| 4,836,986 | 6/1989 | Ogunbiyi et al. | 422/28 |
| 4,861,760 | 8/1989 | Mazuel et al. | 514/54 |
| 4,960,799 | 10/1990 | Nagy | 514/567 |
| 5,037,647 | 8/1991 | Chowhan et al. | 424/78 |
| 5,110,493 | 5/1992 | Cherng-Chyi et al. | 514/413 |
| 5,149,693 | 9/1992 | Cagle et al. | 514/40 |
| 5,149,694 | 9/1992 | Cagle et al. | 514/40 |
| 5,173,507 | 12/1992 | DeSantis et al. | 514/530 |
| 5,188,826 | 2/1993 | Chandrasekaran et al. | 424/78.04 |
| 5,300,287 | 4/1994 | Park | 424/78.04 |
| 5,342,620 | 8/1994 | Chowhan | 424/422 |

FOREIGN PATENT DOCUMENTS

| | | |
|---|---|---|
| WO89/06964 | 8/1989 | WIPO . |
| WO91/09523 | 7/1991 | WIPO . |
| WO94/15597 | 7/1994 | WIPO . |

*Primary Examiner*—Thurman K. Page
*Assistant Examiner*—Sharon Howard
*Attorney, Agent, or Firm*—Patrick M. Ryan

[57] ABSTRACT

Disclosed are storage-stable preserved ophthalmic compositions containing acidic drugs in combination with polymeric quaternary ammonium compounds and boric acid.

5 Claims, No Drawings

PRESERVED OPHTHALMIC DRUG COMPOSITIONS CONTAINING POLYMERIC QUATERNARY AMMONIUM COMPOUNDS

BACKGROUND OF THE INVENTION

This is a divisional application of U.S. patent application Ser. No. 08/340,763 filed Nov. 16, 1994.

The present invention relates generally to ophthalmic compositions. In particular, the present invention relates to the use of a polymeric quaternary ammonium compound and boric acid to provide preserved, storage-stable ophthalmic compositions of acidic drugs.

Ophthalmic formulations generally contain one or more active compounds along with excipients such as surfactants, comforting agents, complexing agents, stabilizers, buffering systems, chelating agents, viscosity agents or gelling polymers and anti-oxidants. Ophthalmic formulations which are intended for multidose use require a preservative.

Organo-mercurials have been used as preservatives in ophthalmic formulations including ophthalmic solutions of acidic drugs. These organo-mercurials include thimerosal, phenylmercuric acetate and phenylmercuric nitrate. Organo-mercurials, however, have limitations due to potential mercury toxicity and poor chemical stability.

Sorbic acid, has also been used to preserve ophthalmic formulations, but it too possesses poor chemical stability as well as poor antimicrobial activity.

Benzalkonium chloride is a widely used preservative in ophthalmic solutions. However, benzalkonium chloride and other quaternary ammonium compounds are generally considered to be incompatible with ophthalmic compositions of drugs with acidic groups, such as nonsteroidal antiinflammatory drugs ("NSAIDS"). These preservative lose their ability to function as they form complexes with the charged drug compounds.

U.S. Pat. No. 5,110,493 discloses stable ophthalmic NSAID formulations which do not contain organo-mercurial preservatives. Instead, the reference NSAID formulations use quaternary ammonium compounds, such as cetyltrimethylammonium bromide, cetylpyridinium chloride and preferably, benzalkonium chloride, and a stabilizing amount of a nonionic surfactant.

PCT application WO 94/15597 discloses the use of lauralkonium chloride, the $C_{12}$ homolog of benzalkonium chloride, in ophthalmic formulations of drugs which are incompatible with benzalkonium chloride. Unlike the mixture of alkyldimethylbenzylammonium chloride known as benzalkonium chloride, this PCT application discloses that lauralkonium chloride is compatible with acidic drug entities; apparently it does not form insoluble ion complexes with the charged drug compounds.

In some cases, the present lack of a single preservative which is safe, stable, and able to meet both the United States Pharmacopoeia (USP) and European Pharmacopoeia (Ph.Eur.) preservative effectiveness requirements for ophthalmic formulations of acidic drugs has forced pharmaceutical companies to develop more than one formulation of the same drug, with each formulation containing a different preservative.

U.S. Pat. No. 4,960,799 discloses storage stable aqueous ophthalmic compositions containing diclofenac, a nonsteroidal antiinflammatory drug, and/or its pharmaceutically acceptable salts. The reference compositions include EDTA as a stabilizing agent, a solubilizer such as polyethoxylated castor oil, and a bacteriostat. The preferred bacteriostats are thimerosal and sorbic acid. No mention is made of any polymeric quaternary ammonium preservative.

The use of Polyquad® and other polymeric quaternary ammonium compounds as a disinfectant and preservative in contact lens care and artificial tear solutions is known. See, for example, U.S. Pat. Nos. 5,037,647; 4,525,346; and 4,407,791. None of these references disclose the use of a polymeric quaternary ammonium compound as a preservative in any formulations of ophthalmic drugs.

SUMMARY OF THE INVENTION

It has now been discovered that the use of a combination of a polymeric quaternary ammonium compound such as Polyquad® and boric acid in ophthalmic compositions of acidic drugs provides a storage-stable composition which has surprisingly good preservative efficacy. This preservative combination of a polymeric quaternary ammonium compound and boric acid is useful in ophthalmic compositions of acidic drugs such as prostaglandins, antifungals, antibacterials, and diagnostic agents. This preservative combination is especially useful in ophthalmic solutions of drugs containing either a carboxyl group such as non-steroidal antiinflammatory drugs (NSAIDS) or a sulfonamide group such as antibacterial drugs.

The present invention also relates to a method for treating or controlling ocular inflammation which comprises topically administering to the affected eye a composition comprising a NSAID, a polymeric quaternary ammonium compound and boric acid.

Among other factors, the present invention is based on the discovery that ophthalmic compositions containing a polymeric quaternary ammonium compound and boric acid may be effectively preserved by the USP and Ph.Eur. preservative effectiveness requirements despite the absence of EDTA, a conventional chelating agent known to potentiate the antimicrobial activity of preservatives such as benzalkonium chloride and sorbic acid.

DETAILED DESCRIPTION OF THE INVENTION

The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium-1, otherwise known as Polyquad® or Onamer M®, with a number average molecular weight between 2,000 to 30,000. Preferably, the number average molecular weight is between 3,000 to 14,000.

The polymeric quaternary ammonium compounds are generally used in the compositions of the present invention in an amount from about 0.00001 to about 3 wt %, preferably from about 0.001 to about 0.1 wt %. Most preferably, the compositions of the present invention contain from about 0.001 to about 0.05 wt % of polymeric quaternary ammonium compounds.

The boric acid used in the compositions of the present invention includes not only boric acid, but also its ophthalmically acceptable acid addition salts, as well as borate-polyol complexes of the type described in U.S. Pat. No. 5,342,620 (Chowhan). In general, an amount from about 0.3 to about 5.0 wt % is used in the compositions of the present invention. It is preferred to use from about 0.3 to about 3.0 wt %, and it most preferred to use from about 0.5 to about 2.0 wt %. The water soluble borate-polyol complexes useful in the compositions of the present invention preferably comprise borate and polyol in a molar ratio between about 1:1 and about 1:10.

Suitable ophthalmic agents which may be included in the compositions of the present invention and administered via the method of the present invention include, but are not limited to, the racemic and enantiomeric forms and ophthalmically acceptable salts, amides, esters and prodrugs of the following types of drugs containing an acidic functionality such as —COOH, —SO$_2$NH$_2$, or SO$_2$NHR groups: anti-glaucoma agents, such as carbonic anhydrase inhibitors, prostaglandins and prostaglandin derivatives; non-steroidal anti-inflammatory agents, including but not limited to those classified as aryl- or heteroaryl- alkanoic acids, such as diclofenac, bromfenac, flurbiprofen, suprofen, ketorolac, indomethacin and ketoprofen; anti-bacterials and anti-infectives, including sulfa drugs, such as sulfacetamide sodium, and beta-lactams such as penicillins and cephalosporins; and diagnostic agents such as sodium fluorescein. Combinations of ophthalmic agents may also be used in the compositions of the present invention.

The compositions of the present invention may additionally include other ophthalmically acceptable components such as comfort enhancing agents, buffers (e.g., phosphate, acetate, carbonate, and citrate), other preservatives (e.g., benzalkonium chloride and individual homologs of benzalkonium chloride, parabens, chlorobutanol, and biguanides such as chlorhexidine and hydroxypropyl methyl biguanide), surfactants (e.g. poloxamers such as Pluronics®; polysorbates such as Tweens®; tyloxapol; sarcosinates such as Hamposyl®; and polyethoxylated castor oils such as Cremophor®), and tonicity agents (e.g., sodium chloride, mannitol, dextrose and xylitol). In addition, other excipients, such as antioxidants, chelating agents and complexing agents may be added to the compositions of the present invention as desired or as necessary.

The compositions of the present invention may also include viscosity modifying agents such as: cellulosic ethers, such as, hydroxypropyl methyl cellulose (HPMC), hydroxyethyl cellulose (HEC), ethyl hydroxyethyl cellulose, hydroxypropyl cellulose, methyl cellulose, and carboxymethyl cellulose; carbomers (e.g. Carbopol®); polyvinyl alcohol; polyvinyl pyrrolidone; alginates; carrageenans; and guar, karaya, agarose, locust bean, tragacanth and xanthan gums. The concentration of such viscosity modifiers will vary between about 0.1 to about 5 wt %, but such formulations will generally have a viscosity between about 10 and about 5000 centipoise.

The ophthalmic compositions of the present invention may additionally contain polymers which will undergo sol-to-gel transition upon exposure to physical or chemical stimuli, such as changes in pH, ion concentration, and/or temperature. Examples of such polymers include but are not limited to: certain carrageenans, and gellan, locust and xanthan gums, such as those described in U.S. Ser. No. 08/108,824 (Lang et al.), U.S. Pat. No. 4,861,760 (Mazuel et al), U.S. Pat. No. 4,136,173 (Pramoda et al), U.S. Pat. No. 4,136,177 (Lin et al.), and U.S. Pat. No. 4,136,178 (Lin et al). The contents of these patent applications and patents relating to the polymers cited above are hereby incorporated by reference herein.

The acidic drugs in the compositions of the present invention may also be encapsulated in microparticles such as microcapsules, microspheres, nanocapsule, nanospheres, and liposomes to improve comfort, and/or provide for sustained release.

The following examples are presented to illustrate further various aspects of the present invention, but are not intended to limit the scope of the invention in any respect.

EXAMPLE 1

The following formulations are representative of preferred compositions of the present invention.

| | Formulation (wt %) | | |
|---|---|---|---|
| Ingredient | A | B | C |
| Sodium Diclofenac | 0.1 | — | — |
| Sulfacetamide Sodium | — | 10 | — |
| Suprofen | — | — | 0.25 |
| HPMC* | 0.1 | 0.1 | 0.1 |
| Tromethamine | 2.0 | 2.0 | 2.0 |
| Boric Acid | 1.2 | 1.2 | 1.2 |
| Vitamin E TPGS** | 3.0 | 3.0 | 3.0 |
| Mannitol | 3.5 | 1.6 | 3.6 |
| Polyquad ® | 0.005 | 0.005 | 0.005 |
| HCl/NaOH | q.s. to pH 7.4 | q.s. to pH 7.4 | q.s. to pH 7.4 |
| Purified Water | q.s. to 100% | q.s. to 100% | q.s. to 100% |

*Hydroxypropyl Methyl Cellulose
**Vitamin E Tocopheryl Polyethylene Glycol 1000 Succinate Preparation The preparation of Formulation A is detailed below. Formulations B and C can be prepared in similar fashion.

Initially, a 10% stock solution of TPGS and a 2% stock solution of HPMC were prepared in water under constant stirring. Heat was applied if necessary to ensure complete dissolution.

To a tared glass vessel containing approximately 40% final weight of purified water was added diclofenac-sodium. This mixture was stirred until the diclofenac was completely dissolved. The following ingredients were then added with stirring in the order given below, and each ingredient was completely dissolved before addition of the next ingredient: stock solution of vitamin E TPGS; tromethamine; boric acid; Polyquad®; mannitol; and stock solution of HPMC.

Water was then added to bring the formulation to 95% of its final weight, and the pH of the formulation adjusted to between 7 and 7.4 using NaOH and/or HCl. Water was then added to bring the final weight to 100%. The resulting formulations were approximately isotonic (above 300 milliOsmoles per kilogram (mOsm/kg)).

EXAMPLE 2

The antimicrobial preservative effectiveness of the polymeric quaternary ammonium compound/boric acid combination of the present invention was determined using an organism challenge test according to the methods described in the United States Pharmacopeia XXII (USP) and European Pharmacopoeia (1994) (Ph.Eur.). Samples were inoculated with known levels of gram-positive (*Staphylococcus aureus* ATCC 6538) and gram-negative (*Pseudomonas aeruginosa* ATCC 9027 and *Escherichia coli* ATCC 8739) vegetative bacteria, yeast (*Candida albicans* ATCC 10231) and mold (*Aspergillus niger* ATCC 16404) and sampled at specified intervals to determine if the antimicrobial preservative system was capable of killing or inhibiting the propagation of organisms purposely introduced into the formulation. The rate or level of antimicrobial activity determined compliance with the USP and/or Ph.Eur. preservative efficacy standards for ophthalmic preparations.

The compendial preservative standards for ophthalmic preparations are presented below:

| Time Pull | USP | Log Reduction of Organism Population | |
|---|---|---|---|
| | | Ph. Eur. A (Target) | Ph. Eur. B (Min) |
| For Bacteria: | | | |
| 6 hours | — | 2 | — |
| 24 hours | — | 3 | 1 |
| 7 days | — | — | 3 |
| 14 days | 3 | — | — |
| 28 days | NI | NR | NI |
| For Fungi: | | | |
| 7 days | — | 2 | — |
| 14 days | NI | — | 1 |
| 28 days | NI | NI | NI |

NR = No organisms recovered
NI = No increase at this or any following time pulls
— = No requirement at this time pull The results of the preservative challenge study conducted on Formulation A are shown below in Table 1. These results illustrate that an ophthalmic formulation of an acidic drug can be globally preserved, that is, can comply with the USP and Ph.Eur. A preservative effectiveness requirements for ophthalmic preparations, using a combination of a polymeric quaternary ammonium compound and boric acid.

TABLE 1

Preservative Challenge Results for Formulation A

| TEST ORGANISM | INITIAL COUNT | Number of Microorganisms Per Milliliter* | | | | | |
|---|---|---|---|---|---|---|---|
| | | 6 Hr | 24 Hr | Day 7 | Day 14 | Day 21 | Day 28 |
| S. aureus | $1.5 \times 10^6$ | <10 | <10 | <10 | <10 | <10 | <10 |
| P. aeruginosa | $1.0 \times 10^6$ | <10 | <10 | <10 | <10 | <10 | <10 |
| E. coli | $1.1 \times 10^6$ | <10 | <10 | <10 | <10 | <10 | <10 |
| C. albicans | $1.2 \times 10^6$ | $6.3 \times 10^5$ | $4.1 \times 10^4$ | $4.4 \times 10^2$ | <10 | <10 | <10 |
| A. niger | $1.3 \times 10^6$ | $1.4 \times 10^6$ | $3.9 \times 10^4$ | $2.5 \times 10^2$ | $8.0 \times 10^1$ | $6.5 \times 10^1$ | <10 |

*Limit of detection: <10 CFU/mL

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for treating or controlling ocular inflammation comprising the topical ocular application of a preserved storage stable ophthalmic composition comprising a therapeutically-effective amount of one or more acidic non-steroidal anti-inflammatory agents, a combination of an antimicrobial polymeric quaternary ammonium compound and boric acid in an amount effective to meet at least the minimum United States Pharmacopeia XXII and European Pharmacopeia (1994) preservative effectiveness requirements, and an ophthalmically acceptable vehicle; provided that the composition does not contain a viscosity-enhancing amount of polyvinyl alcohol.

2. The method of claim 1, wherein the non-steroidal anti-inflammatory agent comprises an aryl- or heteroaryl-alkanoic acid, or an ophthalmically acceptable salt, ester, amide or prodrug thereof.

3. The method of claim 2 wherein the non-steroidal anti-inflammatory agent is selected from the group consisting of diclofenac and its ophthalmically acceptable salts, esters, amides or prodrugs.

4. The method of claim 2 wherein the non-steroidal anti-inflammatory agent is selected from the group consisting of suprofen and its ophthalmically acceptable salts, esters, amides or prodrugs.

5. The method of claim 2 wherein the non-steroidal anti-inflammatory agent is selected from the group consisting of bromfenac and its ophthalmically acceptable salts, esters, amides or prodrugs.

* * * * *